(12) United States Patent
Brady

(10) Patent No.: US 8,556,811 B2
(45) Date of Patent: Oct. 15, 2013

(54) METHOD AND SYSTEM FOR DETERMINING A CEREBROVASCULAR AUTOREGULATION STATE OF A PATIENT

(75) Inventor: Ken M. Brady, Baltimore, MD (US)

(73) Assignee: Johns Hopkins University, Baltimore, MD (US)

(*) Notice: Subject to any disclaimer, the term of this patent is extended or adjusted under 35 U.S.C. 154(b) by 1108 days.

(21) Appl. No.: 12/525,029

(22) PCT Filed: Jan. 4, 2008

(86) PCT No.: PCT/US2008/000170
§ 371 (c)(1),
(2), (4) Date: Jul. 29, 2009

(87) PCT Pub. No.: WO2008/097411
PCT Pub. Date: Aug. 14, 2008

(65) Prior Publication Data
US 2010/0010322 A1    Jan. 14, 2010

Related U.S. Application Data

(60) Provisional application No. 60/899,146, filed on Feb. 2, 2007.

(51) Int. Cl.
*A61B 5/00* (2006.01)
(52) U.S. Cl.
USPC ............ 600/301; 600/485; 600/500; 600/309
(58) Field of Classification Search
USPC ......... 600/300–301, 309–310, 322–324, 364, 600/481, 483–486
See application file for complete search history.

(56) References Cited

U.S. PATENT DOCUMENTS

| | | | | |
|---|---|---|---|---|
| 6,802,812 B1* | 10/2004 | Walker et al. | ................. | 600/309 |
| 2002/0035331 A1* | 3/2002 | Brockway et al. | ............ | 600/486 |
| 2002/0095087 A1* | 7/2002 | Mourad et al. | ................ | 600/442 |
| 2006/0094964 A1* | 5/2006 | Ragauskas et al. | ........... | 600/454 |

FOREIGN PATENT DOCUMENTS

| DE | 103 31 027 A1 | 1/2005 |
|---|---|---|
| WO | WO-2006/050078 A2 | 5/2006 |

OTHER PUBLICATIONS

International Search Report, dated Apr. 17, 2008, mailed May 16, 2008, issued in PCT/US08/000170.
European Search Report issued in counter European Application No. 08713011.8 dated Aug. 13, 2012.
Jaeger et al., "Continuous assessment of cerebrovascular autoregulation after traumatic brain injury using brain tissue oxygen pressure reactivity," Critical Care Medicine, 2006, vol. 34. No. 6, pp. 1783-1788.

(Continued)

*Primary Examiner* — Patricia Mallari
*Assistant Examiner* — Michael D'Angelo
(74) *Attorney, Agent, or Firm* — Venable LLP; Henry J. Daley; Thomas A. Negley

(57) ABSTRACT

A method of diagnosing cerebrovascular autoregulation in a patient includes measuring blood pressure of the patient, measuring, non-invasively, venous oxygen content of the patient's brain substantially simultaneously with the measuring blood pressure, correlating the blood pressure and the venous oxygen content measurements in a time domain, and determining a cerebrovascular autoregulation state of the patient based on the correlating the blood pressure and the venous oxygen content measurements.

25 Claims, 7 Drawing Sheets

(56) References Cited

OTHER PUBLICATIONS

Steinmeier et al., "Slow Rhythmic Oscillations of Blood Pressure, Intracranial Pressure, Microciruculation, and Cerebral Oxygenation," Stroke, 1996 vol. 27, No. 12, pp. 2236-2243.

Lang et al., "Tissue oxygen reactivity and cerebral autoregulation after severe traumatic brain injury," Critical Care Medicine, 2003 vol. 31 No. 1, 267-271.

Schmidt et al., "Computerized Analysis of Cerebral Blood Flow Autoregulation in Humans: Validation of a Method for Pharmacologic Studies," Journal of Cardiovascular Pharmacology, 1990 vol. 15 No. 1, 983-988.

Aaslid et al., Cerebral autoregulation dynamics in humans. Stroke. 1989; 20(1):45-52.

Berkowitz et al., Haemophilus influenzae type B impairment of pial vessel autoregulation in rats. Pediatr Res. 1993; 33(1):48-51.

Czosnyka et al., Continuous assessment of the cerebral vasomotor reactivity in head injury. Neurosurgery. 1997; 41(1):11-7; discussion 17-9.

Czosnyka et al., Monitoring of cerebral autoregulation in head-injured patients. Stroke. 1996; 27(10):1829-1834.

Dawson et al., Serial changes in static and dynamic cerebral autoregulation after acute ischaemic stroke. Cerebrovasc Dis. 2003 16(1):69-75.

Giller, Linearity and non-linearity in cerebral hemodynamics. Med Eng Phys. 2003; 25(8):633-646.

Hiler et al. Predictive value of initial computerized tomography scan, intracranial pressure, and state of autoregulation in patients with traumatic brain injury. J Neurosurg. 2006; 104(5):731-737).

Lam et al., Monitoring of autoregulation using laser doppler flowmetry in patients with head injury. J Neurosurg. 1997; 86(3):438-445.

Laptook et al., Brain blood flow and O2 delivery during hemorrhagic hypotension in the piglet. Pediatr Res. 1983; 17(1):77-80.

Mertineit et al., Nitric oxide, prostaglandins, and impaired cerebral blood flow autoregulation in group B streptococcal neonatal meningitis. Can J Physiol Pharmacol. 2000; 78(3):217-227.

Muizelaar et al., Cerebral blood flow and metabolism in severely head-injured children. part 1: Relationship with GCS score, outcome, ICP, and PVI. J Neurosurg. 1989; 71(1):63-71.

Muizelaar et al., Cerebral blood flow and metabolism in severely head-injured children. part 2: Autoregulation. J Neurosurg. 1989; 71(1):72-76.

O'Rourke et al., Neonatal cerebral oxygen regulation after hypothermic cardiopulmonary bypass and circulatory arrest. Crit Care Med. 2000; 28(1):157-162).

Panerai et al., Assessment of cerebral pressure autoregulation in humans—a review of measurement methods. Physiol Meas. 1998; 19(3):305-338.

Panerai, The critical closing pressure of the cerebral circulation. Med Eng Phys. 2003; 25(8):621-632.

Slater et al., Role of leukocytes in cerebral autoregulation and hyperemia in bacterial meningitis in rabbits. Am J Physiol. 1997; 273(1 Pt 2):H380-6).

Steiner et al., Continuous monitoring of cerebrovascular pressure reactivity allows determination of optimal cerebral perfusion pressure in patients with traumatic brain injury. Crit Care Med. 2002; 30(4):733-738.

Tsuji et al., Cerebral intravascular oxygenation correlates with mean arterial pressure in critically ill premature infants. Pediatrics. 2000; 106(4):625-632.

Vavilala et al., Impaired cerebral autoregulation and 6-month outcome in children with severe traumatic brain injury: Preliminary findings. Dev Neurosci. 2006; 28(4-5):348-353).

\* cited by examiner

METHOD AND SYSTEM FOR DETERMINING A CEREBROVASCULAR AUTOREGULATION STATE OF A PATIENT

CROSS-REFERENCE OF RELATED APPLICATION

This application is a National Stage Application of PCT/US2008/000170, filed Jan. 4, 2008 which claims priority to U.S. Provisional Application No. 60/899,146, filed Feb. 2, 2007, the entire contents of which are hereby incorporated by reference.

BACKGROUND

1. Field of Invention

This application relates to cerebral blood pressure autoregulation and more particularly to devices and methods to diagnose and/or treat cerebrovascular autoregulation in a patient.

2. Discussion of Related Art

The contents of all references, including articles, published patent applications and patents referred to anywhere in this specification are hereby incorporated by reference.

Cerebral pressure autoregulation is defined as the maintenance of a constant cerebral blood flow (CBF) in the face of changing cerebral perfusion pressure (CPP). In health, this process protects the brain during transient changes in the arterial blood pressure (ABP) from diminished or excessive blood flow. Traumatic brain injury (TBI) (Muizelaar J P, Marmarou A, DeSalles A A, et al. Cerebral blood flow and metabolism in severely head-injured children. part 1: Relationship with GCS score, outcome, ICP, and PVI. J Neurosurg. 1989; 71(1):63-71; Muizelaar J P, Ward J D, Marmarou A, Newlon P G, Wachi A. Cerebral blood flow and metabolism in severely head-injured children. part 2: Autoregulation. J Neurosurg. 1989; 71(1):72-76; Vavilala M S, Muangman S, Tontisirin N, et al. Impaired cerebral autoregulation and 6-month outcome in children with severe traumatic brain injury: Preliminary findings. Dev Neurosci. 2006; 28(4-5): 348-353), stroke (Dawson S L, Panerai R B, Potter J F. Serial changes in static and dynamic cerebral autoregulation after acute ischaemic stroke. Cerebrovasc Dis. 2003; 16(1):69-75), meningitis (Berkowitz I D, Hayden W R, Traystman R J, Jones M D, Jr. Haemophilus influenzae type B impairment of pial vessel autoregulation in rats. Pediatr Res. 1993; 33(1): 48-51; Slater A J, Berkowitz I D, Wilson D A, Traystman R J. Role of leukocytes in cerebral autoregulation and hyperemia in bacterial meningitis in rabbits. Am J Physiol. 1997; 273(1 Pt 2):H380-6), cardiopulmonary bypass, and deep hypothermic circulatory arrest (O'Rourke M M, Nork K M, Kurth C D. Neonatal cerebral oxygen regulation after hypothermic cardiopulmonary bypass and circulatory arrest. Crit Care Med. 2000; 28(1):157-162) are examples of insults that have been shown to impair pressure autoregulation and have large-scale clinical impact. An impairment of autoregulation narrows the range of blood pressures at which flow is matched to metabolic needs. Optimal management of CPP for limiting tissue hypoxia at low CPP or edema at high CPP in these patients is critical but difficult to achieve because of limited monitoring capabilities. Despite the recent surge of multimodal neuromonitoring, optimal ABP and CPP have not been defined.

It has been postulated that continuous monitoring of autoregulatory vasoreactivity allows detection of an "optimal CPP" and titration of blood pressure into a range that maximizes vasoreactivity to perturbations in CPP (Steiner L A, Czosnyka M, Piechnik S K, et al. Continuous monitoring of cerebrovascular pressure reactivity allows determination of optimal cerebral perfusion pressure in patients with traumatic brain injury. Crit Care Med. 2002; 30(4):733-738). Autoregulation is measured by quantifying the consequence of changing blood pressure on CBF or its surrogate, and the methods have been extensively reviewed (Panerai R B. Assessment of cerebral pressure autoregulation in humans—a review of measurement methods. Physiol Meas. 1998; 19(3):305-338). Changes in ABP can be induced via drugs, tilt-table, or thigh cuff (Aaslid R, Lindegaard K F, Sorteberg W, Nornes H. Cerebral autoregulation dynamics in humans. Stroke. 1989; 20(1):45-52), or they can occur spontaneously. Using spontaneous changes in ABP is preferable to inducing ABP changes in an unstable patient with an acute intracranial process. However, relying on spontaneous and often subtle ABP fluctuations for this measurement results in an inferior signal-to-noise ratio.

Diverse surrogates of CBF are suitable for continuous monitoring of autoregulation and include flow velocity, measured by transcranial Doppler (Czosnyka M, Smielewski P, Kirkpatrick P, Menon D K, Pickard J D. Monitoring of cerebral autoregulation in head-injured patients. Stroke. 1996; 27(10):1829-1834); red blood cell flux, measured by laser-Doppler (Lam J M, Hsiang J N, Poon W S. Monitoring of autoregulation using laser doppler flowmetry in patients with head injury. J Neurosurg. 1997; 86(3):438-445); parenchymal oxygen tension, measured using a Licox monitor (Lang E W, Czosnyka M, Mehdorn H M. Tissue oxygen reactivity and cerebral autoregulation after severe traumatic brain injury. Crit Care Med. 2003; 31(1):267-271; Jaeger M, Schuhmann M U, Soehle M, Meixensberger J. Continuous assessment of cerebrovascular autoregulation after traumatic brain injury using brain tissue oxygen pressure reactivity. Crit Care Med. 2006; 34(6):1783-1788); and cerebral tissue oxyhemoglobin saturation, measured by transcranial near-infrared spectroscopy (NIRS) (Tsuji M, Saul J P, du Plessis A, et al. Cerebral intravascular oxygenation correlates with mean arterial pressure in critically ill premature infants. Pediatrics. 2000; 106 (4):625-632). Slow waves of intracranial pressure (ICP) reflecting vessel diameter changes in the autoregulatory process have also been correlated to ABP for an index describing autoregulation (Czosnyka M, Smielewski P, Kirkpatrick P, Laing R J, Menon D, Pickard J D. Continuous assessment of the cerebral vasomotor reactivity in head injury. Neurosurgery. 1997; 41(1):11-7; discussion 17-9). An ideal CBF surrogate for an index of autoregulation would be noninvasive and require minimal caregiver attention. It would provide a continuous signal with time resolution sufficiently fine to discriminate changes in frequencies relevant to autoregulation, and that signal would be a close proxy for CBF. There is thus a need for improved methods and devices for diagnosing cerebrovascular autoregulation in patients.

SUMMARY

Further objectives and advantages will become apparent from a consideration of the description, drawings, and examples.

A method of diagnosing cerebrovascular autoregulation in a patient according to an embodiment of the current invention includes measuring blood pressure of the patient, measuring, non-invasively, venous oxygen content of the patient's brain substantially simultaneously with the measuring blood pressure, correlating the blood pressure and the venous oxygen content measurements, and determining a cerebrovascular autoregulation state of the patient based on the correlating the blood pressure and the venous oxygen content measurements.

A system for diagnosing cerebrovascular autoregulation in a patient according to an embodiment of the current invention has a cerebral oximeter arranged proximate an external position of the patient's head, a blood pressure monitoring device attached to the patient, and a signal processing unit in communication with the cerebral oximeter and the blood pressure monitoring device. The cerebral oximeter obtains oxygen content measurements of blood within the patient's brain taken at a plurality of times and outputs an oxygen content signal to the signal processing unit, the blood pressure monitoring device obtains arterial blood pressure measurements of the patient at a plurality of times substantially synchronously with the oxygen content measurements and outputs an arterial blood pressure signal to the signal processing unit, and the signal processing unit calculates a linear correlation coefficient based on the oxygen content signal and the arterial blood pressure signal in the time domain for a plurality of times.

A method of treating a patient according to an embodiment of the current invention includes measuring blood pressure of the patient, measuring, non-invasively, venous oxygen content of the patient's brain substantially simultaneously with the measuring blood pressure, correlating the blood pressure and the venous oxygen content measurements in a time domain, determining a cerebrovascular autoregulation state of the patient based on the correlating the blood pressure and the venous oxygen content measurements, and causing a change of blood pressure of the patient based on the cerebrovascular state of the patient determined based on the correlating.

A data processing unit for use with a system for diagnosing cerebrovascular autoregulation in a patient according to an embodiment of the current invention has at least one signal input port adapted to receive a blood pressure signal from measured blood pressure data from the patient and to receive a venous oxygen content signal from externally measured venous oxygen content data of the patient's brain, a signal correlation component adapted to receive and correlate the blood pressure signal with the venous oxygen content signal to provide a correlation coefficient indicative of a cerebrovascular autoregulation state of the patient, and a signal output port to output the correlation coefficient to indicate the cerebrovascular autoregulation state of the patient based on the correlation coefficient.

A computer readable medium programmed to process data for a system for diagnosing cerebrovascular autoregulation in a patient according to an embodiment of the current invention includes at least one signal receiving component adapted to receive a blood pressure signal from measured blood pressure data from the patient and to receive a venous oxygen content signal from externally measured venous oxygen content data of the patient's brain, a signal correlation component adapted to receive and correlate the blood pressure signal with the venous oxygen content signal to provide a correlation coefficient indicative of a cerebrovascular autoregulation state of the patient, and a signal output component adapted to output the correlation coefficient to indicate the cerebrovascular autoregulation state of the patient based on the correlation coefficient.

BRIEF DESCRIPTION OF THE DRAWINGS

The invention is better understood by reading the following detailed description with reference to the accompanying figures in which:

FIG. 5A is Laser-Doppler flux as a percent of baseline flux at 60 mmHg. FIG. 5B is Cerebrovascular resistance (CVR), calculated as CPP/CBF from the same data set and expressed as a percentage of CVR at CPP of 60 mmHg. FIG. 5C is Cerebral oximetry, measured by NIRS, shown as a percentage of baseline tissue oxyhemoglobin saturation. P<0.0001 by ANOVA for both laser-Doppler flux and oximetry curves. The average breakpoint of autoregulation, determined for individual piglets, was 29.7±5.5 mmHg (vertical dashed line);

DETAILED DESCRIPTION

Figure 1:
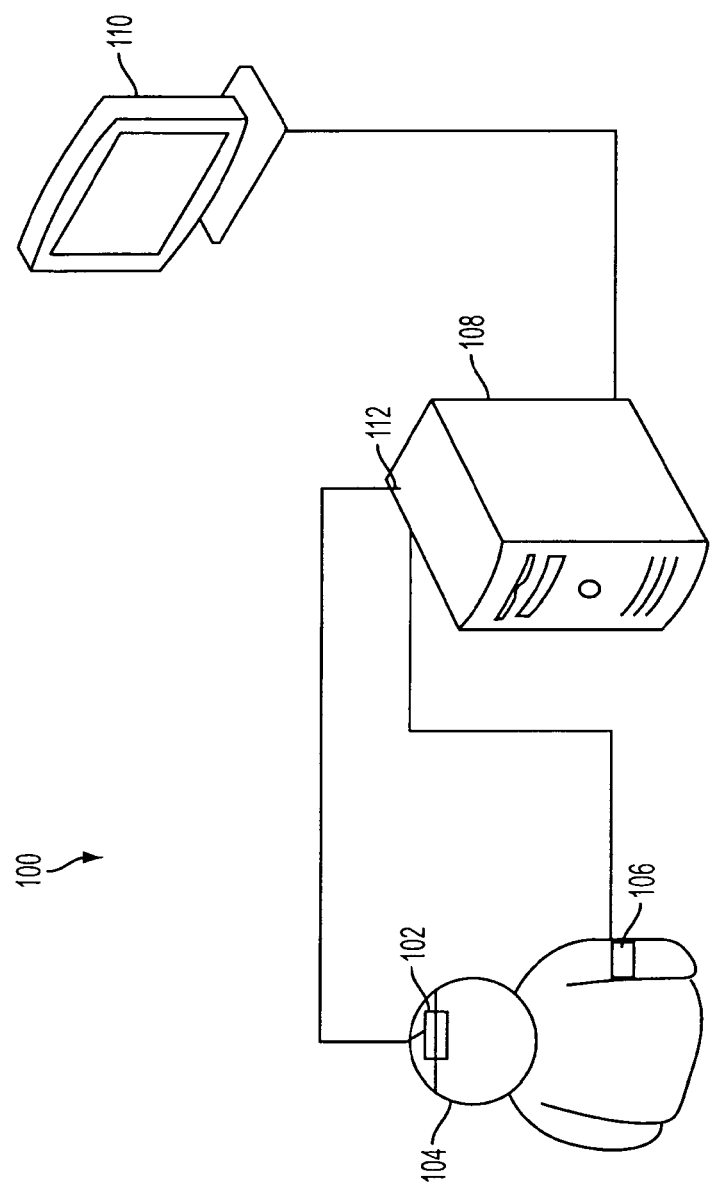
FIG. 1 is a schematic illustration of a system for diagnosing cerebrovascular autoregulation according to an embodiment of the current invention.

In describing embodiments of the present invention illustrated in the drawings, specific terminology is employed for the sake of clarity. However, the invention is not intended to be limited to the specific terminology so selected. It is to be understood that each specific element includes all technical equivalents which operate in a similar manner to accomplish a similar purpose.

Transcranial monitors of cerebral oxygenation using NIRS have attractive features. According to some embodiments of the current invention, we present a novel index of autoregulatory vasoreactivity, the cerebral oximeter index (COx), which is derived from a time-domain analysis that correlates changes in ABP to the output of an NIRS-based monitor of cerebral tissue oxyhemoglobin saturation. Continuous assessment of autoregulation is a promising monitoring method for actively optimizing cerebral perfusion pressure (CPP) in critically ill patients. In one embodiment, this correlation is performed continuously on overlapping epochs of 300 seconds, updated every 60 seconds, and does not require induced changes in ABP to detect autoregulatory failure.

A system for diagnosing cerebrovascular autoregulation of a patient 100 according to an embodiment of the current invention is illustrated schematically in FIG. 1. The system for diagnosing cerebrovascular autoregulation 100 includes a cerebral oximeter 102 that is arranged proximate an external position of the patient's head 104. A blood pressure monitoring device 106 is attached to the patient. A signal processing unit 108 is in communication with the cerebral oximeter 102 and with the blood pressure monitoring device 106. In an embodiment of the invention, the cerebral oximeter obtains oxygen content measurements of blood within the patient's brain. Signals from the cerebral oximeter 102 may be processed internally within the cerebral oximeter 102 and/or processed by the signal processing unit 108. According to an embodiment of the current invention, the oxygen content measurements of blood within the patient's brain is taken a plurality of times by the cerebral oximeter 102 to input an oxygen content signal to the signal processing unit 108.

A blood pressure monitoring device 106 obtains arterial blood pressure measurements of the patient at a plurality of times substantially synchronously with the oxygen content measurements and outputs an arterial blood pressure signal to the signal processing unit 108. The signal processing unit 108 calculates a linear correlation coefficient based on the oxygen content signal and the arterial blood pressure signal in a time domain for a plurality of times. This linear correlation coefficient may be referred to as the cerebral oximeter index (COx) according to some embodiments of the current invention. The oxygen content signals transmitted from the cerebral oximeter 102 to the signal processor 108 are low pass filtered by any one of the cerebral oximeter itself, the signal processing unit 108 or by an intermediate low pass filter in the signal line between the cerebral oximeter 102 and the signal processing unit 108. The blood pressure monitoring device 106, the signal processing unit 108 or an intermediate device in the signal line between blood pressure monitoring device 106 and signal processor 108 provide low pass filtering of the measured blood pressure signal. The blood pressure monitoring device 106 may include an intracranial pressure monitoring device (not shown). An intracranial pressure monitoring device may include a catheter-based device which is surgically inserted into the patient to directly measure intracranial pressure within the patient's brain. The blood pressure monitoring device 106 may include an arterial blood pressure monitoring device that can be selected from available arterial blood pressure monitoring devices. In an embodiment of the current invention, the cerebral oximeter 102 can be a near-infrared spectrometer.

The system for diagnosing cerebrovascular autoregulation 100 may also include a display unit 110 that is in communication with the signal processing unit 108 to display the linear correlation coefficient values calculated by the signal processing unit with respect to other biophysical data of the patient. For example, the display unit may display the linear correlation coefficients calculated as a function of arterial blood pressure. Alternatively, the signal processing unit 108 may determine the cerebral perfusion pressure based on the difference between the arterial blood pressure and the intracranial pressure and provide signals to the display unit 110 to display the calculated linear correlation coefficients as a function of the cerebral perfusion pressure.

The cerebral oximeter 102, the blood pressure monitoring device 106, the display unit 110 and the signal processing unit 108 may be connected by physical wires or other suitable means such as optical or wireless data communications. The signal processing unit 108 can be a stand alone physical component, or may be added as a component to other systems such as to a rack system. The signal processing unit 108 is not necessarily limited to processing only signal data. It may include generally data processing capabilities. In addition, the signal processing operations of the signal processing unit 108 may be hard-wired or may be implemented by programming the signal processing unit.

Figure 2:
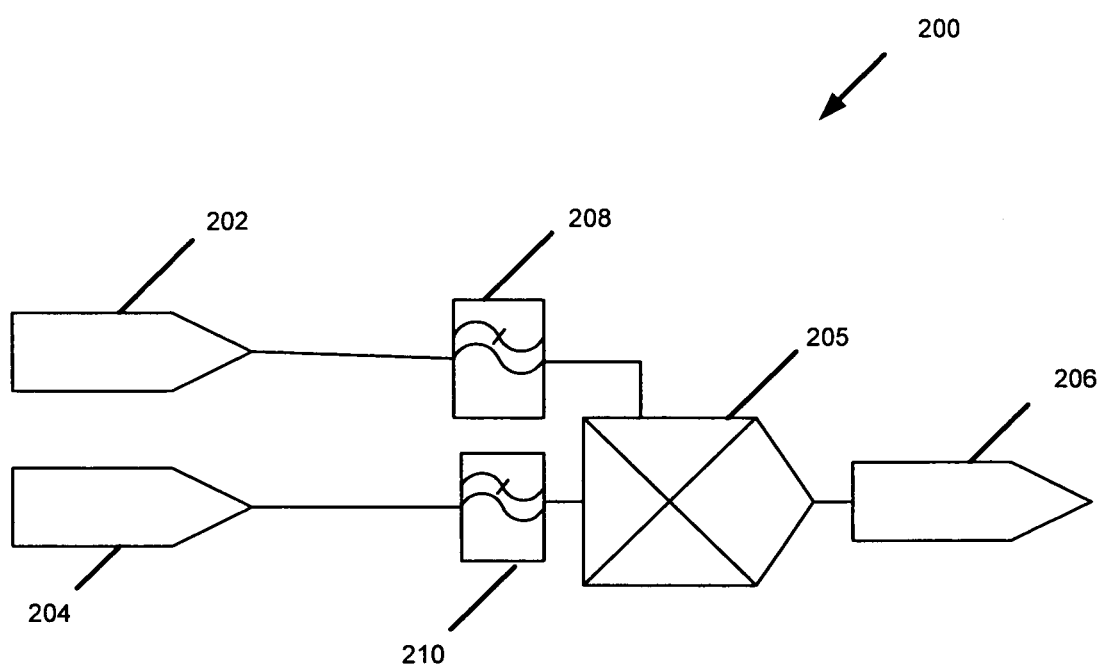
FIG. 2 is a schematic diagram to help explain a method of diagnosing and/or treating cerebrovascular autoregulation in a patient according to an embodiment of the current invention.

FIG. 2 is a schematic illustration that facilitates the description of a method of diagnosing cerebrovascular autoregulation in a patient 200 according to an embodiment of the current invention. The method of diagnosing cerebrovascular autoregulation 200 includes measuring blood pressure of a patient 202, measuring, non-invasively, venous oxygen content of the patient's brain 204 substantially simultaneously with the measuring arterial blood pressure 202, and correlating the blood pressure and the venous oxygen content measurements in a time domain 205. In an embodiment of the current invention, a cerebrovascular autoregulation state of the patient is determined 206 based on the correlating of the blood pressure 202 and venous oxygen content 204 measurements. The blood pressure signals 202 are low pass filtered 208 according to an embodiment of the current invention. The low pass filtering 208 allows slow variations of blood pressure signals to pass through the filter while filtering out the more rapid variations in blood pressure signals. The low pass filtering 208 may be implemented with either hardware or software according to various embodiments of the current invention. Furthermore, the low pass filtering can be analog low pass filtering or digital low pass filtering, depending on whether an analog or digital signal is being processed. In one embodiment of the current invention, the blood pressure signal may be sampled to provide a digital signal and the low pass filtering can be accomplished by selecting a desired sampling frequency.

In an embodiment of the current invention, the venous oxygen content measurements may be low pass filtered 210 prior to being correlated 205 with the blood pressure signals. In one embodiment of the current invention, the venous oxygen content data may be obtained by sampling substantially synchronously with sampling of a blood pressure data to provide a digital signal. In this case, the low pass filtering 210 may be achieved by selecting the sampling frequency at a desired sampling frequency. However, the general aspects of this invention are not limited to only digital signal processing and are not limited to only digital low pass filtering. The blood pressure measurement data 202 may correspond to arterial blood pressure or may correspond to cerebral perfusion pressure determined by also measuring intracranial pressure. The venous oxygen content data may be obtained, for example, by measuring differential absorption of near-infrared radiation directed into the patient's brain from a source of near-infrared radiation disposed proximate an external position of the patient's head.

Another embodiment of the current invention is directed to a method of treating a patient that includes measuring blood pressure of the patient, measuring, non-invasively, oxygen content of the patient's brain substantially simultaneously with measuring blood pressure, and correlating the blood pressure measurements and oxygen content measurements in a time domain. The blood pressure measurement data may correspond to arterial blood pressure or may correspond to cerebral perfusion pressure determined by also measuring intracranial pressure. A cerebrovascular autoregulation state of the patient is determined based on the correlating of the blood pressure and venous oxygen content measurements and a change of blood pressure or cerebral perfusion pressure is effected based on the determined cerebrovascular autoregulation state of the patient.

Another embodiment of the current invention is directed to a data processing unit for use with a system for diagnosing cerebrovascular autoregulation in a patient. For example, the data processing unit may be similar to or the same as the data processing 108 described with reference to the system for diagnosing cerebrovascular autoregulation 100 in FIG. 1. The data processing unit 108 includes at least one signal input port 112 that is adapted to receive blood pressure signals from measured blood pressure data from the patient and to receive venous oxygen content signals from externally measured venous oxygen content data of the patient's brain. The data processing unit 108 also has a signal correlation component adapted to receive and correlate the blood pressure signal and venous oxygen content signal to provide a linear correlation coefficient indicative of a cerebrovascular autoregulation state of the patient. The data processing unit 108 also includes a signal output port 114 to output the linear correlation coefficient to be further processed, stored and/or displayed. The data processing unit 108 may include a low-pass filter to filter the blood pressure data and may include a low-pass filter to filter the venous oxygen content data in an embodiment of the current invention. In alternative embodiments, the blood pressure data and/or the venous oxygen content data may have already been filtered prior to being received by the data processing unit. The blood pressure data may include arterial blood pressure in some embodiments of the current invention. The data processing unit 108 may also be adapted to receive intracranial pressure signals from measured intracranial pressure of the patient. This may be received through the same input port 112, or through an additional data input port. Similarly, the arterial blood pressure signal may be transmitted to the data processing unit 108 through the same signal input port 112 as the venous oxygen content signals or may be provided through a separate port. The broad concepts of the invention are not limited to any particular number of data input and output ports or whether data is multiplexed for input and/or output over any of the data ports. In addition, the signal input/output ports may be electrical, optical, or wireless data input/output ports.

In another embodiment of the current invention, a computer readable medium is programmed to process data from a system for diagnosing cerebrovascular autoregulation in a patient. The computer readable medium is programmed to receive and process at least one signal from blood pressure measurements and a signal from venous oxygen content measurements and to calculate a linear correlation coefficient based on the correlation between the arterial blood pressure data and the venous oxygen content data in a time domain. The computer readable medium is programmed to output the linear correlation coefficient to provide information upon which cerebrovascular autoregulation of the patient can be determined.

EXAMPLES

We hypothesized that the COx according to an embodiment of the current invention would be sensitive for autoregulatory failure due to hypotension in a piglet model of the infant brain and measured the COx continuously in piglets, while slowly lowering their ABP below the breakpoint of autoregulation, as determined by laser-Doppler flowmetry. We determined the sensitivity and specificity of the COx for detecting the loss of autoregulation caused by hypotension. We also tested the COx against a similar, but invasive method, the laser-Doppler index (LDx), which utilizes a linear correlation coefficient between ABP and laser-Doppler flux measured in the frontoparietal cortex. We hypothesized that the COx and LDx would show agreement as measurements of autoregulatory vasoreactivity despite their distinct origins.

Methods and Materials

All procedures were approved by the Johns Hopkins University Animal Care and Use Committee and conformed to the standards of animal experimentation of the National Institutes of Health.

Anesthesia

Piglets (n=6), aged 3-8 days old and weighing 2.2-3.9 kg, were anesthetized with inhalation of 5% isoflurane, 50% nitrous oxide, and balance of oxygen. A tracheotomy was performed and mechanical ventilation was instituted. Peripheral intravenous access was obtained for the administration of vecuronium (5-mg bolus and 2-mg/hr infusion) and fentanyl (25-μg bolus and 25-μg/hr infusion). Isoflurane was decreased to 0.5% for the duration of the experiment, and the fentanyl was titrated between 10-50 μg/hr for a target heart rate lower than 190 and normotension during surgery. During the recording period, when blood pressure was actively lowered, fentanyl was infused at 50 μg/hr (20 μg/kg/hr for most of the piglets) and tachycardia was permitted as a response to the preload reduction. Isoflurane remained at 0.5%, and the nitrous oxide remained at 50% of the inspired gas. Thus, the anesthetic for the recording period was primarily narcotic based, with a sub-anesthetic supplementation of inhalational agent. This combination was chosen to ensure the comfort of the animal and reduce the effect of inhaled anesthetic on cerebrovascular responsiveness.

Piglets were kept on a warming pad to maintain brain and rectal temperature at 38.5-39.5° C. Ventilation was adjusted to keep pH at 7.35-7.45 and $P_aO_2$ at 200-300 mmHg.

Surgery

The femoral veins were cannulated bilaterally for placement of a central venous line for drug infusion and pressure monitoring and a 5 Fr esophageal balloon catheter (Cooper Surgical, Trundall, Conn.), which was used for interruption of venous return to the heart to produce hypotension. The femoral artery was cannulated for placement of a pressure and blood gas monitoring line. A craniotomy was performed 4 mm lateral and rostral to the bregma at midline for placement of an external ventricular drain catheter, which was transduced for ICP monitoring. An additional craniotomy was performed 4 mm lateral and rostral to the first craniotomy for placement of a laser-Doppler probe (Moor Instruments, Devon, U.K.), which was advanced across the incised dura mater to contact the surface of the frontoparietal cortex. The probe was positioned to avoid high baseline flux values associated with placement over large vessels and was secured in place by a rubber washer cemented to the skull. A third craniotomy in the occipital skull lateral to the midline was used to place a brain temperature probe. Skin was reapplied to the skull, and the wound was sutured closed for heat retention and to create conditions for which the cerebral oximeter had been calibrated.

Oximetry Probe Placement

The INVOS (in vivo optical spectroscopy) pediatric cerebral oximeter probe (Somanetics, Troy, Mich.) was placed above the eye, across the frontal and parietal cortex, opposite the side of craniotomies, with the emitting diode situated 1 cm lateral to midline to avoid the sagittal sinus. The cerebral specificity of the probe was then tested with a $CO_2$ challenge: ventilation was increased to reduce end-tidal $CO_2$ by at least 10 mmHg. Cerebral oximetry was compared with oximetry obtained from a probe that was placed over the kidney. Cerebral oximetry values decreased (1.2±0.1%/mmHg; ±SD), whereas the renal oximetry values were static (0.0±0.1%/mmHg).

Signal Sampling

Waveforms from the pressure transducers (ABP, ICP), the laser-Doppler probe, and the INVOS cerebral oximeter were sampled from an analog-to-digital converter by ICM+ software (Cambridge University, Cambridge, UK) at 60 Hz. The time resolution of INVOS oximetry is 4 seconds. These signals were then time-integrated as non-overlapping 10-second mean values, which is equivalent to applying a moving average filter with a 10-second time window and resampling at 0.1 Hz. This operation eliminates high-frequency noise from the respiratory and pulse frequencies of the animals but, according to the Nyquist theorem, allows detection of oscillations and transients that occur below 0.05 Hz. CPP was calculated as the difference between the 10-second mean values of ABP and ICP.

Calculation of the Laser-Doppler and Cerebral Oximeter Indices

A continuous, moving Pearson's correlation coefficient was performed between the CPP and laser-Doppler to render the LDx or between the CPP and the cerebral oximeter output to render the COx. Consecutive, paired, 10-second averaged values from 300-second duration were used for each calculation, incorporating 30 data points for each index. These indices were calculated and recorded every 60 seconds from overlapping time periods.

Blood Pressure Lowering and Construction of the Autoregulation Curve

Figure 3:
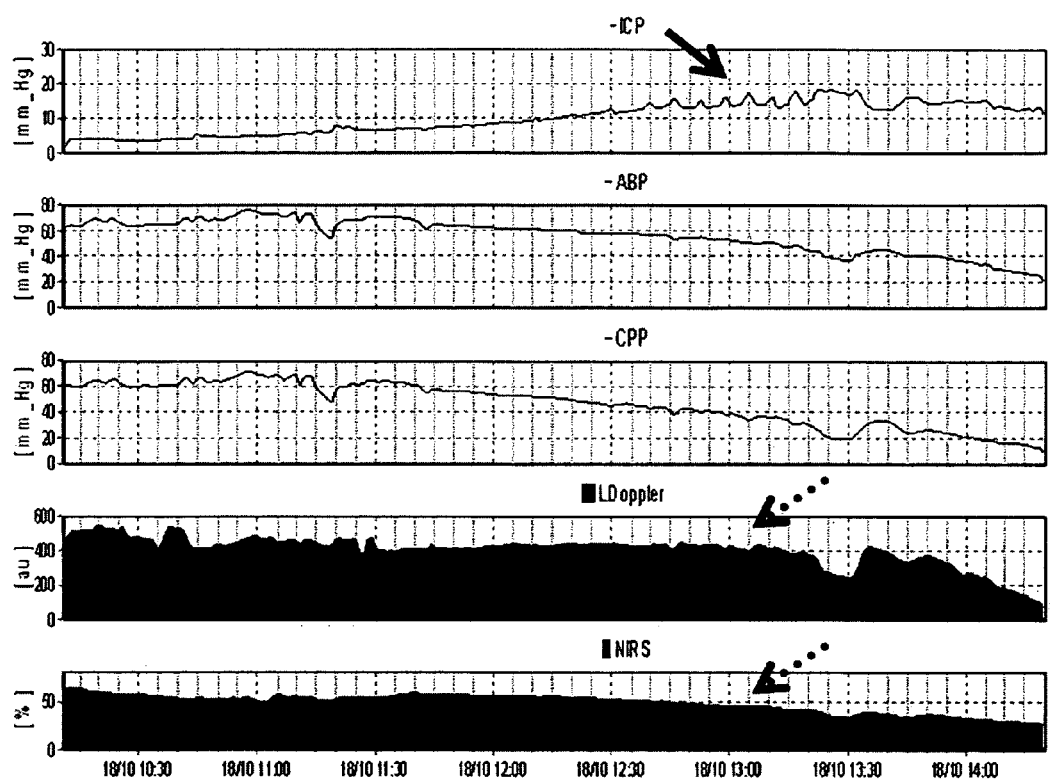
FIG. 3 shows time trends of recordings from a single piglet. ICP, ABP, and CPP are shown in mmHg; laser-Doppler red blood cell flux is in arbitrary units; and cerebral oximetry (NIRS) is expressed as a percent saturation of hemoglobin. Time on the x-axis covers a spread of 4 hours and 10 minutes. Slow "B" waves of ICP are seen in the top tracing at low ABP prior to failure of autoregulation (solid arrow). The oximeter readout showed a more gradual decline relative to the laser-Doppler flux, which had a pattern more indicative of autoregulation (dashed arrows). A similar trend was observed in all 6 piglets.

With the above-mentioned monitors in place, the balloon catheter in the inferior vena cava was gradually inflated by infusion of saline from a syringe pump to slowly lower ABP to ~10 mmHg over 4-5 hours (FIG. 3). Cerebral oximetry, laser-Doppler flux, COx, and LDx values were recorded every 60 seconds in real time and simultaneously sorted according to the CPP at which they were collected. Hypotension was induced over a prolonged period to permit sufficient time for spontaneous changes in CPP to occur over each range of quasi-steady state CPP and thus provide an adequate signal/noise ratio for calculating COx.

Determination of the Steady-State Autoregulatory Breakpoint

A scatter plot of laser-Doppler flow versus CPP was made for all of the data for each piglet using SigmaStat software (Systat, San Jose, Calif.). The CPP that demarcated two regression lines with the lowest combined residual squared error was determined and defined as the autoregulatory breakpoint. In addition, relative changes in cerebrovascular resistance (CVR) were calculated as a percent of the baseline CPP/laser-Doppler flux ratio.

Receiver-Operator Characteristics

Prism software (GraphPad, San Diego, Calif.) was used to determine the receiver-operator characteristics (ROC) of the COx and LDx. To do so, the averaged index values at each CPP for each piglet were dichotomized above and below the CPP breakpoint, as derived from the laser-Doppler flow autoregulatory relationship for each piglet.

Comparison of the LDx and COx

Regression analysis and linear correlation of the COx against the LDx was performed with Prism software and with Bland-Altman plots, using LDx-COx and COx/LDx against the mean. This analysis was performed for all paired indices collected and again for averaged values collected on the same piglet at the same CPP.

Confirmation of the Spectral Range of Autoregulation in the Piglets

Using ICM Plus software, a cross-spectral analysis of coherence was performed, using ABP as input and either laser-Doppler flux or cerebral oximetry as output. Coherence at frequencies that ranged from 1 Hz to 0.001 Hz was compared between the hypotensive and normotensive states. These data are not presented formally but were used to structure the sampling and calculation parameters for the time-domain analysis presented (see Discussion).

Results

Arterial pH, $P_aCO_2$, and brain temperature were within the normal physiologic range during normotension (CPP>50 mmHg), moderate hypotension above the autoregulatory breakpoint (CPP30-50 mmHg), and severe hypotension below the autoregulatory breakpoint (CPP<30 mmHg), as shown in Table 1. To prevent $CO_2$-reactivity from affecting the oximeter readings, we sought to keep a constant $P_aCO_2$, but a small decrement was noted in each piglet as cardiac output fell to critical levels. It is unlikely that this small decrement introduced a bias into the autoregulatory indices, as they evaluate pressure passivity over discrete 300-second intervals that are relatively stationary with respect to the $P_aCO_2$.

Figure 4:
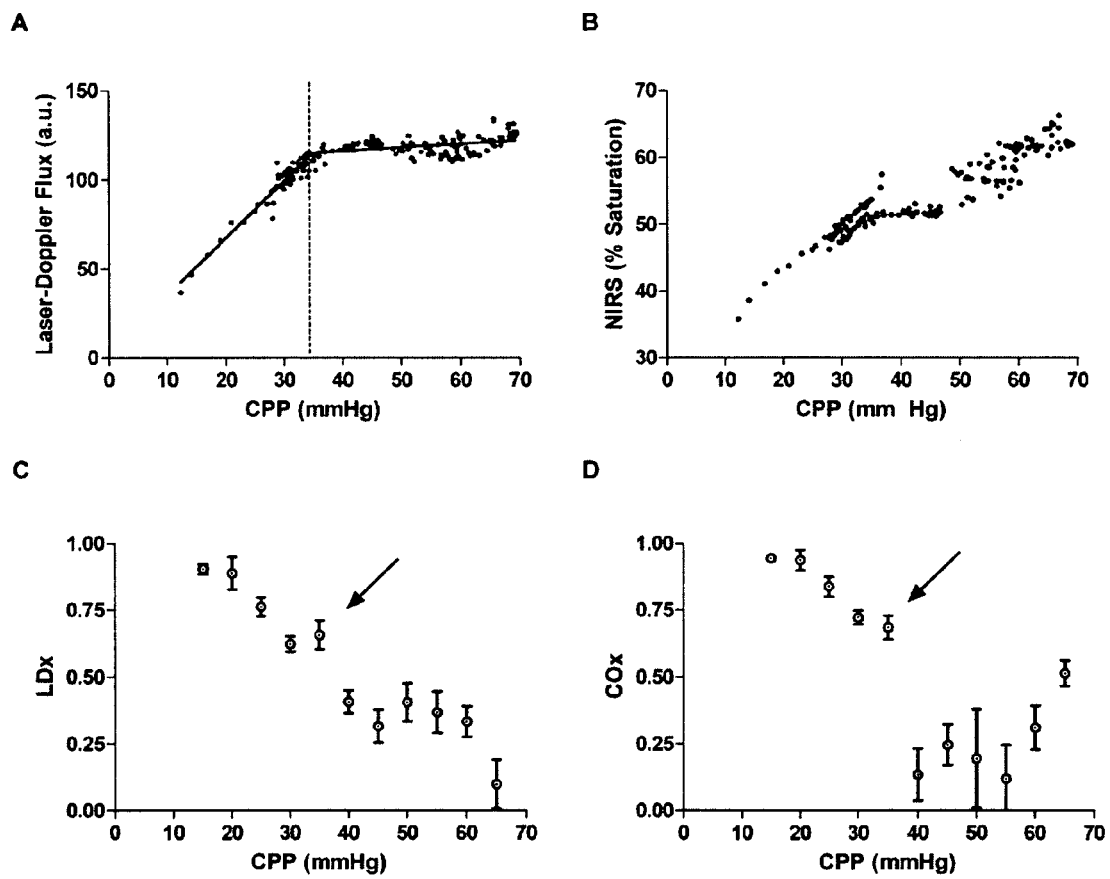
FIG. 4A shows a steady-state autoregulatory graph of laser-Doppler flux versus CPP in a single piglet. The breakpoint was defined as the division that resulted in regression lines with the lowest combined residual squared error (34 mmHg in this piglet).
FIG. 4B shows near-infrared spectroscopy (NIRS)-derived cerebral oximetry versus CPP. This relationship did not have the obvious plateau seen with laser-Doppler flux. However, the laser-Doppler index (LDx, ±SE, FIG. 4C) and the cerebral oximetry index (COx, FIG. 4D) were concordant, showing low values above a CPP of 35 mmHg and high values below a CPP of 35 mmHg (arrows)

An example of the autoregulatory assessment for a single piglet is shown in FIG. 4. The lower limit of autoregulation of laser-Doppler flow was easily identified from the intersection of two regression lines that minimized the overall sum of the residual squared errors (FIG. 4A). Interestingly, the plot of cerebral oximetry as a function of CPP was not as well characterized by an inflection point (FIG. 4B). However, the LDx and COx both showed a sharp increase at the autoregulatory threshold in the animal presented (FIGS. 4C and 4D).

Figure 5:
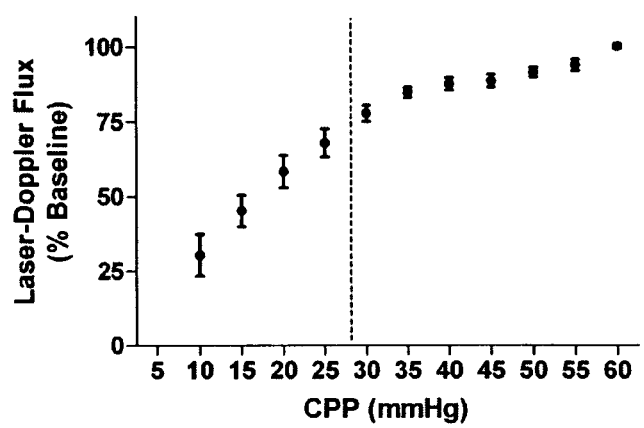
FIGS. 5A-5C show static autoregulation curves derived from 6 piglets (±SE).
Figure 5:
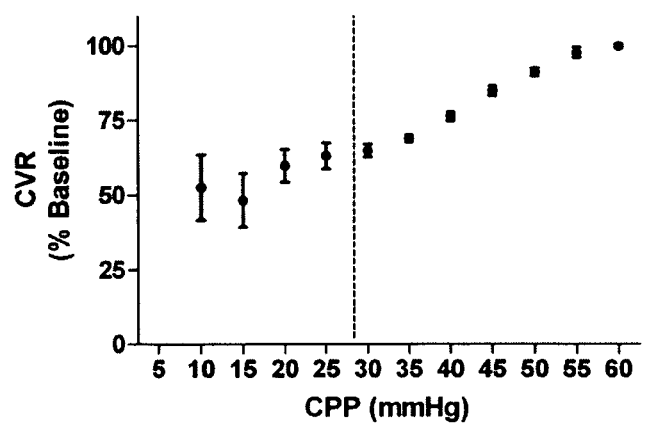
Figure 5:
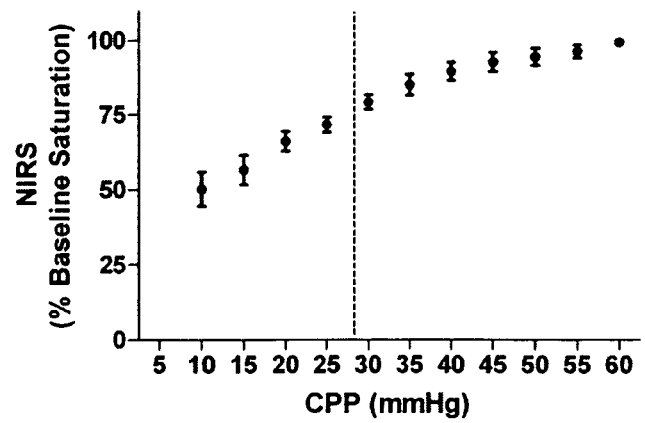
Figure 6:
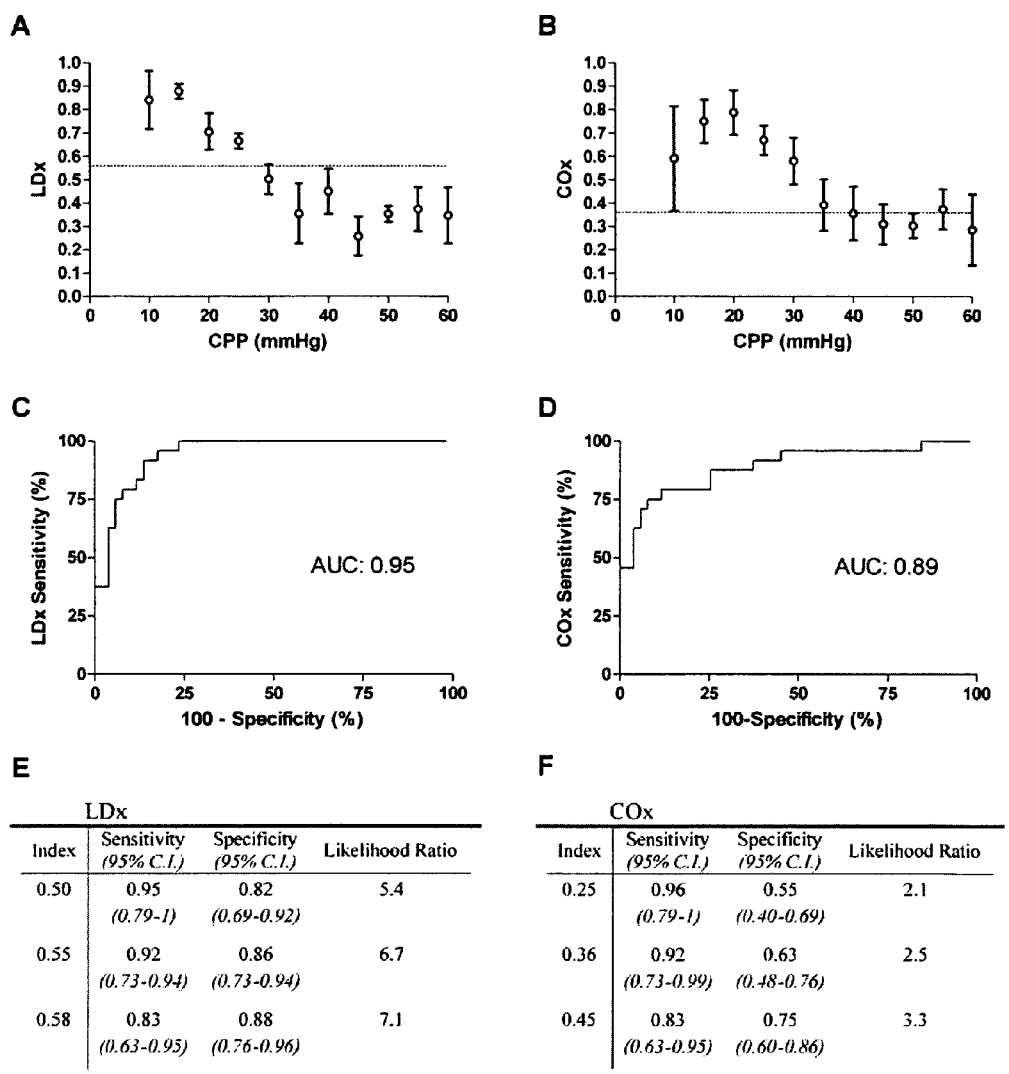
FIG. 6A shows average LDx and FIG. 6B shows COx for the six piglets (±SE) stratified by the CPP at which they were measured. The horizontal dashed line shows the 90% sensitivity cutoff for detecting autoregulatory failure. The receiver-operator characteristics are compared between the LDx (FIG. 6C) and COx (FIG. 6D) calculations of 6 piglets, averaged for each 5 mmHg increment of CPP. AUC is area under the curve. Confidence intervals for sensitivity and specificity and likelihood ratios are tabulated for different sensitivity levels for each index.

Data combined from 6 piglets for laser-Doppler flow, relative CVR, and cerebral oximetry are shown in FIG. 5. The average breakpoint was 29.7±5.5 mmHg, which compares well with previous reports of piglet autoregulatory curves (Laptook A R, Stonestreet B S, Oh W. Brain blood flow and O2 delivery during hemorrhagic hypotension in the piglet. Pediatr Res. 1983; 17(1):77-80; Mertineit C, Samlalsingh-Parker J, Glibetic M, Ricard G, Noya F J, Aranda J V. Nitric oxide, prostaglandins, and impaired cerebral blood flow autoregulation in group B streptococcal neonatal meningitis. Can J Physiol Pharmacol. 2000; 78(3):217-227). Graded decreases in relative CVR were evident as CPP decreased to 30 mmHg, and further decreases were diminished at CPP values below 30 mmHg. The average LDx and COx increased when CPP was below 30 mmHg (FIGS. 6A and 6B). Knowing the steady-state autoregulatory breakpoint for each piglet permitted determination of the ROC for LDx and COx. Not surprisingly, because the LDx is a derivative of the laser-Doppler flow, the LDx performed better than the COx, but both accurately described the breakpoint well. The areas under the ROC curves were 0.95 for the LDx (FIG. 6C) and 0.89 for the COx (FIG. 6D). Summaries of the sensitivity, specificity, and likelihood ratios for cutoff values of the two indices are shown in FIG. 6. In general, sensitivity was superior to specificity for both indices: all piglets showed abnormal autoregulatory vasoreactivity by both the COx and the LDx when hypotensive, but many also showed episodic disruptions of one or both indices in the normotensive or moderately hypotensive range.

Figure 7:
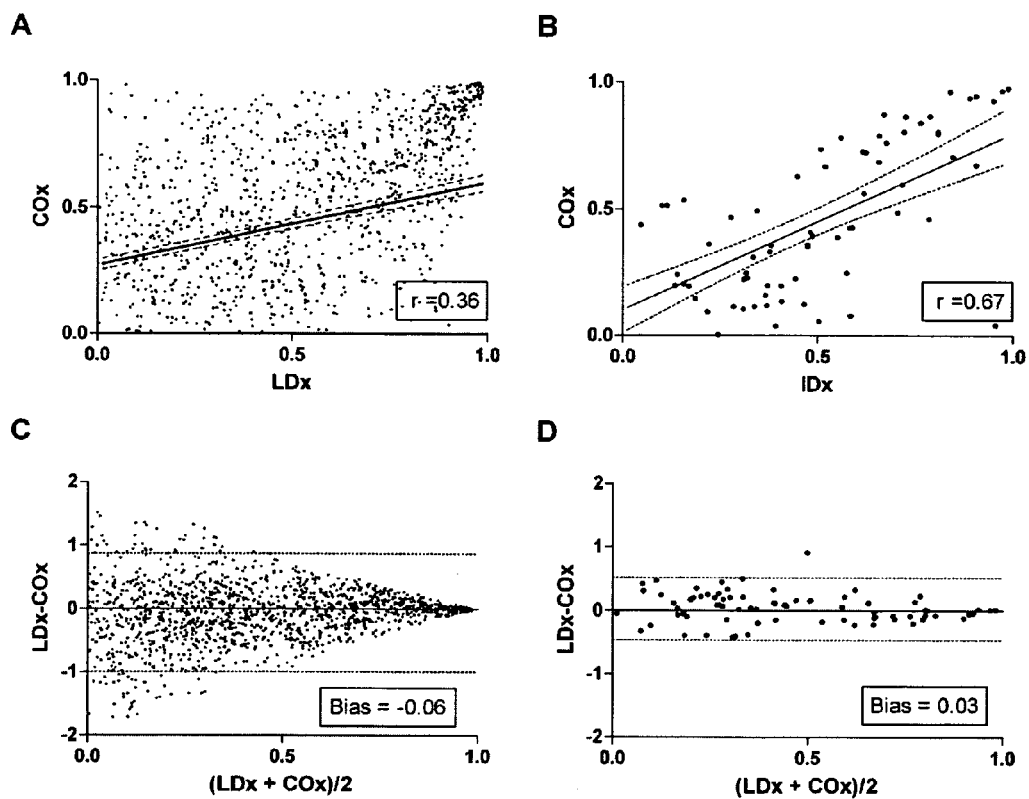
FIGS. 7A-7D show linear regression (7A, 7B) and Bland Altman plots (7C,7D) comparing LDx and COx for all data points (7A,7D) and averaged data points taken at the same CPP for each piglet (7B,7D). Agreement improves substantially by averaging, which implies a low signal-to-noise ratio for individual index measurements. Dashed lines are 95% confidence intervals (regression) and 95% limits of agreement (Bland-Altman).

The linear correlation and Bland-Altman comparison of the COx and LDx are shown in FIG. 7. Agreement between the indices was limited when evaluated on a minute-to-minute basis (Pearson's r=0.36). Agreement improved greatly with averaging of the values stratified according to the 5-mmHg incremental bins of CPP at which they were collected (Pearson's r=0.67). The Bland-Altman method showed no bias across the range of measurements (bias –0.06 for all values measured, 0.03 for averaged values) and showed the improvement in agreement when values were averaged at the same CPP.

Discussion

The present results show that time-domain correlation of ABP and cerebral oximetry can quantify spontaneous autoregulatory vasoreactivity, and the resultant index is sensitive for loss of autoregulation caused by hypotension in a piglet model. This method has several features that are attractive for clinical application. The COx output is continuous and updated every 60 seconds, as configured in the animals presented. The COx can be displayed at the bedside as a function of clinical parameters, such as CPP, showing the effect of changes in management on the autoregulatory process. The COx requires no intracranial surgery for calculation and can use spontaneous changes in ABP, obviating the need to induce rapid changes in ABP in an unstable patient.

An important task in the development of the COx was the determination of relevant periods for waveform sampling. Our rationale for this determination, a discussion of the limitations of the COx, and a description of the potential clinical application of the COx are presented below.

Considerations of the Frequencies Chosen for Analysis in the COx

Associative relationships between ABP and CBF surrogates can be dynamically assessed by methods that fall into two broad categories: analysis in the frequency domain and analysis in the time domain. Frequency-domain analysis (based on coherence, transfer function, or phase shifts) is well suited for regular, periodic waves or induced changes in ABP in an otherwise static system. This analysis has assumptions of linearity and stationarity that are not always strictly present in a biologic system (Giller C A, Mueller M. Linearity and non-linearity in cerebral hemodynamics. Med Eng Phys. 2003; 25(8):633-646). Time-domain analysis can be performed as a linear correlation between low-pass filtered ABP and CBF waves, as presented here with the COx and LDx, but this filtering limits the spectral range of the test. For such an analysis to describe autoregulation, the clinically relevant wavelength periods that encompass CPP and oximetry correlations caused by autoregulatory failure must be known.

Our focus on frequencies between 0 and 0.04 Hz is based on three suppositions. First, and most important, is the work of Tsuji et al., who used a frequency-domain analysis of coherence between NIRS and ABP in premature infants (Tsuji M, Saul J P, du Plessis A, et al. Cerebral intravascular oxygenation correlates with mean arterial pressure in critically ill premature infants. Pediatrics. 2000; 106(4):625-632). They identified a subgroup with a high coherence at frequencies lower than 0.01 Hz and found an increased incidence of intraventricular hemorrhage in this group, which was hypothesized to have been the result of impaired autoregulation. This finding suggests that these low frequencies are useful in describing correlations of ABP and CBF that can be clinically relevant. A second argument for the chosen frequencies comes from the ICP-derived index of autoregulation (PRx), which correlates slow "B" waves of ICP with ABP. The PRx has been shown to associate with outcome in head-injured patients and is thought to be a marker of the autoregulatory process (Czosnyka M, Smielewski P, Kirkpatrick P, Laing R J, Menon D, Pickard J D. Continuous assessment of the cerebral vasomotor reactivity in head injury. Neurosurgery. 1997; 41(1):11-7; discussion 17-9). In our database, these slow ICP waves were too sporadic to appear with clarity in a Fourier transfer analysis, but they were identified in the raw waveforms obtained from the piglets and their duration range was measured to be 65-300 seconds, which would correspond to frequencies between 0.015 and 0.003 Hz. The final rationale comes from a coherence analysis of the ABP and NIRS waveforms in the piglets used in this study. In waveforms obtained at blood pressures below the lower limit of autoregulation, we found coherence at frequencies lower than 0.04 Hz, and especially at frequencies lower than 0.02 Hz. This coherence was absent from waveforms obtained during normotension.

Given the above findings, we desired to resolve waveform relationships that occurred at frequencies lower than 0.04 Hz (periods>25 seconds). At the same time, we wished to prevent the aliasing of noise from the high-frequency range, which included the respiratory and heart rate frequencies. The respiratory rate was ~0.3 Hz (3-second periodicity). Thus, time averaging of 10-second periods suppressed this noise and preserved resolution at the chosen frequencies.

Limitations of the COx

Understanding the sources of error in the sensitivity and specificity of the COx can lead to strategies for improvement. Using transient and spontaneous changes in ABP decreases the signal-to-noise ratio, when compared to methods that induce large changes in blood pressure over brief periods of time. Two obvious solutions can be chosen for increasing the signal/noise ratio: (a) increasing the sampling time for calculating each index, or (b) averaging multiple discreet calculations of the indices together. We chose the second option because it has the same data smoothing effect but is more useful, as it allows for sorting according to clinically relevant variables (CPP, temperature, blood gases, sedation states, etc.). These variables are likely to be more stationary over a 5-minute period than over 20- or 60-minute periods. Our experimental design sought to control these variables and thereby isolate the effect of changing CPP, but minor deviations in $PaCO_2$ did occur. Dynamic changes in cerebral $O_2$ consumption could affect COx. We assume that the fentanyl, nitrous oxide, and isoflurane anesthesia provided a stable $O_2$ consumption over each 300-second period used to calculate COx.

Others have dealt with the signal-to-noise ratio problem by incorporating exclusion rules in the index calculation that require a specific range of CPP. For instance, epochs of time with less than 10 mmHg change in ABP could be excluded from analysis (Lam J M, Hsiang J N, Poon W S. Monitoring of autoregulation using laser doppler flowmetry in patients with head injury. J Neurosurg. 1997; 86(3):438-445). The introduction of bias caused by excluding periods with stable blood pressure has not been determined, and this method was not practical for our experimental model because of the slow stable reduction in ABP that was achieved. Deficiencies of sensitivity that occurred with either the LDx or the COx were largely limited to the extreme hypotensive state, just prior to the death of the animal, as can be seen with the increased variability at the CPP of 10 in FIG. 4. The data set was incomplete in this range, consisting of a limited recording time and only 3 animals due to difficulties encountered in sustaining cardiac function. It is possible that ABP lower than the critical closing pressure caused low and static CBF and cerebral oxygenation that did not change with small ABP fluctuations (Panerai R B. The critical closing pressure of the cerebral circulation. Med Eng Phys. 2003; 25(8):621-632). Such a static CBF state could give the false appearance of intact autoregulation by the COx or LDx assessments. Dynamic decreases in cerebral $O_2$ consumption could also add to the variability of these indices. Blood pressure in this range is not important for the clinical questions targeted.

Clinical Implications of the COx

An important goal of clinical monitoring of autoregulation is the delineation of care parameters that improve autoregulation. Patients with intact autoregulation are more likely to survive neurologic injury, and commutative logic would suggest that improving autoregulation would improve neurologic recovery and survival (Steiner L A, Czosnyka M, Piechnik S K, et al. Continuous monitoring of cerebrovascular pressure reactivity allows determination of optimal cerebral perfusion pressure in patients with traumatic brain injury. Crit Care Med. 2002; 30(4):733-738; Czosnyka M, Smielewski P, Kirkpatrick P, Laing R J, Menon D, Pickard J D. Continuous assessment of the cerebral vasomotor reactivity in head injury. Neurosurgery. 1997; 41(1):11-7; discussion 17-9; Hiler M, Czosnyka M, Hutchinson P, et al. Predictive value of initial computerized tomography scan, intracranial pressure, and state of autoregulation in patients with traumatic brain injury. J Neurosurg. 2006; 104(5):731-737). Tools that can quantify autoregulation at the clinical bedside will allow for testing of this hypothesis. Because the COx is not invasive, it can be used for patients with acute neurologic processes who do not or cannot undergo neurosurgical intervention, including patients with moderate head-trauma, stroke and meningitis, and patients undergoing cardiopulmonary bypass for corrective heart surgery or exchange transfusion for acute chest syndrome. In addition, the COx could be a valuable adjunct to the monitoring of pressure autoregulation in the setting of severe head injury when added to other indices derived from invasive monitoring.

The embodiments illustrated and discussed in this specification are intended only to teach those skilled in the art the best way known to the inventors to make and use the invention. Nothing in this specification should be considered as limiting the scope of the present invention. The above-described embodiments of the invention may be modified or varied, and elements added or omitted, without departing from the invention, as appreciated by those skilled in the art in light of the above teachings. It is therefore to be understood that, within the scope of the claims and their equivalents, the invention may be practiced otherwise than as specifically described.

TABLE 1

Physiologic Parameters (mean ± SEM) Measured during Progressive Hypotension

| Physiologic parameter | CPP >50 mmHg | CPP 30-50 mmHg | CPP <30 mmHg |
|---|---|---|---|
| Arterial pH | 7.42 ± 0.02 | 7.35 ± 0.06 | 7.39 ± 0.02 |
| $P_aCO_2$ (mmHg) | 37.0 ± 4.9 | 34.5 ± 3.5 | 33.0 ± 1.6 |
| $P_aO2$ (mmHg) | 229 ± 29 | 208 ± 39 | 231 ± 35 |
| Hematocrit (%) | 25 ± 5 | 23 ± 3 | 22 ± 3 |
| Brain Temperature (° C.) | 38.7 ± 0.8 | 38.6 ± 0.8 | 38.6 ± 0.7 |

I claim:

1. A method of diagnosing cerebrovascular autoregulation in a patient, comprising:
   measuring blood pressure of said patient;
   measuring, non-invasively, venous oxygen content of said patient's brain substantially simultaneously with said measuring blood pressure;
   correlating said blood pressure and said venous oxygen content measurements in a time domain; and
   determining, using a data processing unit, a cerebrovascular autoregulation state of said patient based on said correlating said blood pressure and said venous oxygen content measurements.

2. A method of diagnosing cerebrovascular autoregulation in a patient according to claim 1, wherein said measuring blood pressure comprises low-pass filtering said blood pressure measurements to allow measurement of only time-dependent blood pressure variations having a frequency lower than a threshold frequency.

3. A method of diagnosing cerebrovascular autoregulation in a patient according to claim 1, wherein said measuring blood pressure comprises sampling values of said patient's arterial blood pressure at a substantially periodic sampling rate, wherein said substantially periodic sampling rate is selected to have a value to provide low-pass filtering of said arterial blood pressure to allow measurement of only time-dependent blood pressure variations having a frequency lower than a threshold frequency.

4. A method of diagnosing cerebrovascular autoregulation in a patient according to claim 3, wherein said measuring, non-invasively, venous oxygen content comprises sampling values of said patient's venous oxygen content synchronously with said sampling values of said patient's blood pressure.

5. A method of diagnosing cerebrovascular autoregulation in a patient according to claim 4, wherein said correlating said arterial blood pressure and said venous oxygen content measurements comprises calculating a linear correlation coefficient having a value that is indicative of said autoregulation state of said patient.

6. A method of diagnosing cerebrovascular autoregulation in a patient according to claim 5, further comprising displaying said linear correlation coefficient as a function of arterial blood pressure to provide a pattern that is indicative of said autoregulation state of said patient.

7. A method of diagnosing cerebrovascular autoregulation in a patient according to claim 5, further comprising measuring an intracranial pressure of said patient and displaying said linear correlation coefficient as a function of a cerebral perfusion pressure of said patient to provide a pattern that is indicative of said autoregulation state of said patient, said cerebral perfusion pressure being calculated as a difference between said arterial blood pressure and said intracranial pressure.

8. A method of diagnosing cerebrovascular autoregulation in a patient according to claim 1, wherein said measuring, non-invasively, venous oxygen content of said patient's brain comprises measuring differential absorption of near-infra-red radiation directed into said patient's brain from a source of near-infra-red radiation disposed proximate an external position of said patient's head.

9. A system for diagnosing cerebrovascular autoregulation in a patient, comprising:
   a cerebral oximeter arranged proximate an external position of said patient's head;
   a blood pressure monitoring device adapted to be attached to said patient; and a signal processing unit in communication with said cerebral oximeter and said blood pressure monitoring device, wherein said cerebral oximeter obtains oxygen content measurements of blood within said patient's brain taken at a plurality of times and outputs an oxygen content signal to said signal processing unit, wherein said blood pressure monitoring device obtains arterial blood pressure measurements of said patient at a plurality of times substantially synchronously with said oxygen content measurements and outputs an arterial blood pressure signal to said signal processing unit, and wherein said signal processing unit calculates a linear correlation coefficient based on said oxygen content signal and said arterial blood pressure signal in a time domain for a plurality of times.

10. A system for diagnosing cerebrovascular autoregulation in a patient according to claim 9, wherein at least one of said cerebral oximeter or said signal processor provides low-pass filtering of said oxygen content signal.

11. A system for diagnosing cerebrovascular autoregulation in a patient according to claim 9, wherein at least one of said blood pressure monitoring device or said signal processor provides low-pass filtering of said blood pressure signal.

12. A system for diagnosing cerebrovascular autoregulation in a patient according to claim 9, wherein said oximeter is a near-infra-red spectrometer.

13. A system for diagnosing cerebrovascular autoregulation in a patient according to claim 9, further comprising a display unit to display said linear correlation coefficient values with respect to other biophysical data of said patient.

14. A system for diagnosing cerebrovascular autoregulation in a patient according to claim 13, wherein said other biophysical data of said patient with respect to which said linear correlation coefficient is displayed is at least one of arterial blood pressure or cerebral perfusion pressure of said patient.

15. A system for diagnosing cerebrovascular autoregulation in a patient according to claim 9, wherein said blood pressure monitoring device comprises an arterial blood pressure monitoring device.

16. A system for diagnosing cerebrovascular autoregulation in a patient according to claim 15, wherein said blood pressure monitoring device comprises an intracranial pressure monitoring device.

17. A system for diagnosing cerebrovascular autoregulation in a patient according to claim 16, wherein said signal processing unit calculates cerebral perfusion pressure of said patient based on measured arterial blood pressure and measured intracranial pressure of said patient.

18. A system for diagnosing cerebrovascular autoregulation in a patient according to claim 17, wherein said other biophysical data of said patient with respect to which said linear correlation coefficient is displayed is cerebral perfusion pressure of said patient.

19. A method of treating a patient, comprising:
measuring blood pressure of said patient;
measuring, non-invasively, venous oxygen content of said patient's brain substantially simultaneously with said measuring blood pressure;
correlating said blood pressure and said venous oxygen content measurements;
determining, using a data processing unit, a cerebrovascular autoregulation state of said patient based on said correlating said blood pressure and said venous oxygen content measurements; and
causing a change of blood pressure of said patient based on said cerebrovascular state of said patient determined based on said correlating.

20. A method of treating a patient according to claim 19, wherein said causing a change of said blood pressure comprises administering a substance to said patient that causes said patient's body to react with a change in blood pressure.

21. A data processing unit for use with a system for diagnosing cerebrovascular autoregulation in a patient, comprising:
at least one signal input port adapted to receive an arterial blood pressure signal from measured arterial blood pressure data from said patient and to receive a venous oxygen content signal from externally measured venous oxygen content data of said patient's brain;
a signal correlation component adapted to receive and correlate said arterial blood pressure signal with said venous oxygen content signal to provide a correlation coefficient indicative of a cerebrovascular autoregulation state of said patient; and
a signal output port to output said correlation coefficient to indicate said cerebrovascular autoregulation state of said patient based on said correlation coefficient.

22. A data processing unit for use with a system for diagnosing cerebrovascular autoregulation in a patient according to 21, further comprising a low pass filter adapted to filter at least one of said measured arterial blood pressure data and said externally measured venous oxygen content data prior to being correlated by said signal correlation component.

23. A data processing unit for use with a system for diagnosing cerebrovascular autoregulation in a patient according to 21, wherein said at least one signal input port is adapted to also receive an intracranial pressure signal from measured intracranial pressure data from said patient.

24. A data processing unit for use with a system for diagnosing cerebrovascular autoregulation in a patient according to 23, further comprising a cerebral perfusion pressure calculating unit adapted to calculate cerebral perfusion pressure based on said measured arterial blood pressure data and said measured intracranial pressure data.

25. A non-transient computer readable medium programmed to process data for a system for diagnosing cerebrovascular autoregulation in a patient, comprising:
at least one signal receiving component adapted to receive a blood pressure signal from measured blood pressure data from said patient and to receive a venous oxygen content signal from externally measured venous oxygen content data of said patient's brain;
a signal correlation component adapted to receive and correlate said arterial blood pressure signal with said venous oxygen content signal to provide a correlation coefficient indicative of a cerebrovascular autoregulation state of said patient; and
a signal output component adapted to output said correlation coefficient to indicate said cerebrovascular autoregulation state of said patient based on said correlation coefficient.

* * * * *